United States Patent [19]

Frazier et al.

[11] Patent Number: 4,980,152
[45] Date of Patent: Dec. 25, 1990

[54] ORAL PREPARATION

[75] Inventors: William F. Frazier; Angle B. Casillan, both of Overland Park, Kans.

[73] Assignee: Marion Laboratories, Kansas City, Mo.

[21] Appl. No.: 82,432

[22] Filed: Aug. 6, 1987

[51] Int. Cl.$^5$ ............................ A61K 7/18; A61K 7/20
[52] U.S. Cl. .......................................... 424/52; 424/53
[58] Field of Search ................ 424/53, 149, 52; 564/3

[56] References Cited

U.S. PATENT DOCUMENTS

| | | | |
|---|---|---|---|
| 3,574,824 | 4/1971 | Echeandia et al. | 424/50 |
| 3,657,413 | 4/1972 | Rosenthal | 424/81 |
| 4,431,631 | 2/1984 | Clipper et al. | 424/53 |
| 4,522,805 | 6/1985 | Gordon | 424/52 |
| 4,528,180 | 7/1985 | Schaeffer | 424/53 |
| 4,537,778 | 8/1985 | Clipper et al. | 424/53 |
| 4,684,517 | 8/1987 | Clipper et al. | 424/53 |
| 4,687,663 | 8/1987 | Schaeffer | 424/53 |

OTHER PUBLICATIONS

Stafford–Miller, CA. 76:158373c, 1972 of Gt. Br. 1,267,618, Mar. 22, 1972.
Firma Dr. Scheller Duro Dont., CA. 72:24645b, 1970 of Fr. 1,559,617, Mar. 14, 1969.
Krezanuski, CA. 80:149031v, 1974 of Ger. Offen DE 2 340568, Feb. 21, 1974.

*Primary Examiner*—Shep K. Rose
*Attorney, Agent, or Firm*—Robert S. Beiser

[57] ABSTRACT

An aqueous oral preparation is provided having from about 0.5% to about 10% by weight of a peroxide compound such as hydrogen peroxide or urea peroxide and from about 0.01% to about 2% by weight of a compound providing fluoride or fluoride-containing ions in an aqueous composition. The compound may further include a thickening agent, such as carboxy polymethylene, a non-ionic surfactant, such as Pluronic brand poloxamer, buffering agents, stabilizers, glycerine, sweeteners, and deionized filterd water as a solvent. A variety of flavoring and/or coloring agents may also be added. A stable compatable and highly effective dental preparation is thereby provided.

20 Claims, No Drawings

ORAL PREPARATION

BACKGROUND OF THE INVENTION

The present invention relates to an oral preparation and especially to an aqueous peroxide mouthwash, mouth rinse solution, gel, paste, or foam containing a fluoride.

It has long been recognized in the art that hydrogen peroxide and other peroxide-containing agents are effective in curative and/or prophylactic treatments with respect to caries, dental plaque, gingivitis, periodontitis, mouth orthodontic appliance lesions, perpetic stomatitis and the like. Peroxide-containing agents in the oral cavity exert a chemo-mechanical action generating thousands of tiny oxygen bubbles produced by interaction with tissue and salivary enzymes. The swishing action of a mouth rinse enhances this inherent chemo-mechanical action. Such action has been recommended for delivery of other agents into infected gingival crevices. Peroxide mouth rinses and other oral preparations prevent colonization and multiplication of anaerobic bacteria known to be associated with periodontal disease.

Peroxide-containing gels or paste are indicated and/or desirable where it is required to selectively treat areas for more than a few seconds. Such gels and pastes tend to remain at the site of application for a time sufficient for the peroxide to manifest its maximum effectiveness. The addition of a fluoride-containing compound would provide anti-caries activity. With the cleansing ability of the peroxide, the fluoride-containing compound would have maximum opportunity to reach the tooth surface and gingival margins.

However, it has been found in the past that most peroxide compounds, by interaction with other common excipients therein, tend to be unstable in storage, continuously losing the capacity to release active or nascent oxygen over relatively short periods of time, and tend to diminish or destroy the desired function of such excipients. Among such excipients are flavors and coloring agents added to enhance the acceptability of the preparation. In addition, it has been found that many peroxide compounds tend to generate gaseous emissions, thereby rendering them unsuitable for storage in a closed container.

Accordingly, it is an object of the present invention to provide oral preparations which will not be subject to one or more of the aforementioned disadvantages and deficiencies.

Still another object of the present invention is the provision of an oral preparation having a pleasant flavor and/or color and enhanced stability in storage.

Still a further object of the present invention is provision of an oxygenating oral preparation containing an anti-caries agent such as fluoride.

SUMMARY OF THE INVENTION

According to the present invention, there is provided an aqueous oral preparation containing approximately by weight from about 0.5% to about 10% by weight of a peroxide compound and from about 0.01% to about 2% by weight of a compound providing fluoride or fluoride-containing ions in the aqueous composition. In a preferred embodiment the peroxide compound comprises hydrogen peroxide although urea peroxide compounds may also be utilized. The hydrogen peroxide comprises from about 0.5 to about 4% by weight of the composition. Alternatively, the urea peroxide comprises from about 1% to about 10% by weight of the composition. The compound may further include a thickening agent such as Carbopol brand carboxypolymethelyne. A non-ionic surfactant such as Pluronic F127 brand poloxamer may also be included in a concentration of from about 10% to about 28% by weight. The composition may also include Natrosol brand alkali soluble cellulose ethers in a concentration of from about 0.5% to about 3% by weight for uses as a viscosity increasing agent. Similarly, from about 0.5% to about 1% by weight potassium phosphate may be utilized as a buffering agent. From about 0.1% to about 5% by weight sodium hydroxide may also be added as a buffering agent with potassium phosphate. Similarly, from about 1% to about 20% by weight glycerine may be added for use as a bulking agent. From about 0.2% to about 0.3% by weight sodium saccharine may be added as a artificial sweetener. In a preferred embodiment from about 11% to about 64% by weight deionized filtered water is added as a solvent.

An additional feature of the invention is the wide variety of flavorings that may be added in a concentration of from about 0.25% to about 2.5% by weight. Such flavorings may include glyoxide flavor, spearmint, mint, sodium citrate, citric acid anhydrous, sodium citrate dihydrate, lime terpenes and methyl eucalyptol, as well as other commonly known flavoring compounds for oral compositions. The aforementioned flavoring compounds have been found to be satisfactorily stable and compatible in the presence of peroxide compounds.

As described above, the compositions of the present invention may contain other functional agents such as anti-caries agents and the like. Flourine providing anti-caries compounds present in these solutions may be partially or fully water soluble. They are characterized by their ability to release flourine containing ions in water and by substantial freedom from reaction with other compounds of the oral preparation. Although sodium fluoride and stannous fluoride are specified, other fluorine compounds may be utilized. The amount of the fluorine-providing compound is dependent to some extent on the type of compound, its solubility and the type of oral preparation, but it must be a non-toxic amount. Although about 0.2% by weight of fluoride compound is preferred a maximum of up to about 1% may be utilized.

Although saccharine, especially sodium saccharine, in concentrations of about 0.01% to about 5% by weight is preferred, other sweetener compounds such as xylitol, aspartame and the like, may be utilized. The pH of the solution and other paste and gels of the present invention generally range from about four to about seven, and preferably about five. Generally, the pH may be from about 4 to about 7.

DETAILED DESCRIPTION OF THE PREFERRED EMBODIMENT

The invention may be put into practice in various ways and a number of specific embodiments will be described to illustrate the invention with reference to the accompanying examples:

EXAMPLE 1

Gly-oxide fluoride dentifrice soft type

Purpose: To prepare a "Pearl-Drops" toothpaste like product containing $H_2O_2$. This was a composition prepared for consistency but contains no fluoride or flavor.

| FORMULA | % w/w |
|---|---|
| Hydrogen Peroxide (20%) | 20.00 |
| Pluronic F127 - Poloxamer | 15.00 |
| Carbopol 934P (5% w/w) - Carboxypolymethyleme | 6.50 |
| Triethanolamine (10% w/w) | 3.25 |
| Deionized $H_2O$, Filtered | 55.25 |
| TOTAL | 100.00 |

Method: (1) Mixed $H_2O_2$, Pluronic, and $H_2O$. Placed in freezer overnight, then mixed well; (2) added Carbopol Solution and mixed until no globules were seen; and (3) mixed in triethanolamine.

Result: A clear, colorless viscous solution was obtained that when squeezed from a bottle onto a toothbrush, tended to remain on top sinking into bristles, only slowly.

The composition had a pH of 6.00.

Viscosity—spindle 4; speed 2.5; reading 60; visc.—48,000 cps.

EXAMPLE 2

Gly-oxide dentifrice soft type with sodium-fluoride

Purpose: To determine proper carbopol concentration for a dentifrice containing NaF (i.e., reduces visc. of carbopol gels).

| FORMULA | A | B | C | D |
|---|---|---|---|---|
| Hydrogen Peroxide (20%) | 20.0 | 20.0 | 20.0 | 20.0 |
| Pluronic F127 | 15.0 | 15.0 | 15.0 | 15.0 |
| Carbopol 934P | 1.5 | 1.25 | 1.0 | .75 |
| Triethanolamine (10%) | 15.0 | 12.5 | 10.0 | 7.5 |
| NaF | 0.2 | 0.2 | 0.2 | 0.2 |
| Water, DI Filtered | 48.3 | 51.05 | 53.80 | 56.55 |
| TOTAL | 100.00 | 100.00 | 100.00 | 100.00 |

Method: (1) Dissolve Carbopol in water and $H_2O_2$; (2) disperse Pluronic F127 in step one and put in freezer overnight; (3) thaw and mix well (some globules remain or may be Carbopol salting out; (4) add NaF; and (5) add triethanolamine.

Result: The resulting composition had the following properties:

| RESULTS | pH | SPINDLE SPEED | VISC | APPEARANCE ON BRUSH |
|---|---|---|---|---|
| A | 5.76 | TA & TB @ 5 | 31,400 cps | Too Thick |
| B | 5.83 | TA & TB @ 5 | 18,280 | Acceptable |
| C | 5.53 | TA @ 5 & TB @ 5 | 9,960 | Too Thin |
| D | 5.58 | TA @ 5 & #3 @ 10 | 4,270 | Too Thin |

EXAMPLE 3

Gly-oxide dentifrice soft gel soft type with NaF

Purpose: To prepare a prototype

| FORMULA | % w/w | LOT |
|---|---|---|
| $H_2O_2$ (20%) | 20.0 | 100 |
| Pluronic F127 | 15.0 | 75 |
| Carbopol 934P | 1.2 | 6 |
| Triethanolamine (10%) | 12.0 | 60 |
| NaF | 0.2 | 1 |

| FORMULA | % w/w | LOT |
|---|---|---|
| Water, DI FILTERED | 51.6 | 258 |
| TOTAL | 00.0 | 500 |

Method: (1) Dissolve carbopol in $H_2O_2$ and 75% of water; (2) Dissolve NaF in remaining $H_2O$ and add to Step 1; (3) Pass Pluronic through a #16 screen an disperse in Step 2. Place in freezer for one hour; and (4) Mix above well and add triethanolamine solution.

Result: A viscous, clear, colorless gel with many air bubbles. pH—5.43, viscosity—21,800 cps (TA, S—5, R—54.5) The gel dispenses easily from a Gly-oxide bottle and stays on a brush like Pearl Drops toothpaste.

EXAMPLE 4 gly-oxide dentifrice

| FORMULA | % w/w | LOT |
|---|---|---|
| $H_2O_2$, 20% | 20.0 | 180 g |
| Pluronic F127 | 28.0 | 252 |
| Citric Acid, Anhydrous | 0.5 | 4.5 |
| Na Citrate, Dihydrate | 0.25 | 2.25 |
| NaF | 0.2 | 1.8 |
| Glycerine | 10.0 | 90.0 |
| Na Saccharin | 0.2 | 1.8 |
| Methyl Paraben | 0.05 | 0.45 |
| Aromalok 180816 Sample Flavor | 2.0 | 18.0 |
| Water DI, Filtered | 38.8 | 349.2 |
| TOTAL | 100 | 900 |

Method: (1) Dissolve citric acid, Na Citrate, NaF, Na Saccharin and Methyl Paraben in the $H_2O_2$, water, and Glycerine; (2) Dispense Aromalok and Pluronic; (3) Place in freezer; and (4) Remove from freezer and mix well then package in tubes.

Result: Typical Pluronic gel with flavor.

EXAMPLE 5

Gly-oxide dentifrice

Purpose: To prepare peroxide dentifrice for pH determination.

| FORMULA | A | B | C | D | E | F |
|---|---|---|---|---|---|---|
| Urea | 6.83 | | | | | |
| $H_2O_2$, 35% | 11.5 | | | | | |
| Pluronic F127 | 25.0 | | | | | |
| Citric Acid, Anhydrous | 0.5 | | SAME | | | |
| Sodium Citrate, Dihyrous | 1.5 | | | | | |
| Sodium Fluoride | — | 0.2 | — | 0.2 | — | — |
| Stannous Fluoride | — | — | — | — | 0.4 | 0.4 |
| Water, DI Filtered | QS | QS | QS | QS | QS | QS |
| TOTAL | 100 | 100 | 100 | 100 | 100 | 100 |

Method: (Prepare 400 g ea.): (1) Dissolve Citric Acid, Sodium Citrate, and Urea in water; (2) Mix with Darco G-60 (Urea containing formulas only at 2 g/l.) and filter thru Whatman #40 filter paper; (3) Dissolve fluoride, if called for above, mix in Pluronic and freeze overnight; (4) Thaw, add $H_2O_2$; and (5) Determined initial pH and placed on test at R.T., 37° C. and 45° C. Tested weekly for 2 months.

| | |
|---|---|
| A - pH 5.15 | D - pH 5.02 |
| B - pH 5.15 | E - pH 4.80 |

-continued

| C - pH 4.95 | F - pH 4.72 |
|---|---|

Result: All were clear gels

EXAMPLE 6

Gly-oxide dentifrice

Purpose: To prepare and test the stability of colored Gly-Oxide Dentifrice gels.

| FORMULA % w/w | A | B | C | D | E | F | G | H | I |
|---|---|---|---|---|---|---|---|---|---|
| Urea | 6.83 | | | | | | | | |
| $H_2O_2$ | 4.00 | | | | | | | | |
| Pluronic F127 | 25.00 | | | | | | | | |
| Citric Acid, Anhy. | 0.50 | | | | | | | | |
| Sodium Citrate, Dihy. | 1.50 | | | | | | | | |
| Sodium Fluorid | 0.20 | | | | | | | | |
| FDC Yellow #6 | — | .0007 | | | | | .003 | | .003 |
| FDC Red #40 | — | | .003 | | | | | | |
| FDC Red #3 | — | | | .003 | | | .003 | .003 | |
| FDC Blue #1 | — | | | | .02 | | | | .003 |
| FDC Green #3 | — | | | | | .003 | | | |
| Water DI | | QS | QS | QS | QS | QS | QS | QS | QS |
| TOTAL | 100 | 100 | 100 | 100 | 100 | 100 | 100 | 100 | 100 |
| pH | 5.3 | 5.2 | 5.2 | 5.2 | 5.2 | 5.2 | 5.2 | 5.2 | 5.2 |

Method: (1) Dissolve Citric Acid, Na Citrate, and Urea in water; (2) Mix c Darco G60 Urea (2g/liter) for 15 minutes; (3) SUCTION filter through #40 Whatman; (4) Dissolve NaF and disperse Pluronic; put in freezer; (5) Thaw, add $H_2O_2$ and color (as an $H_2O$ conc). Packaged in clear glass jars. Placed on physical stability test at R.T., 37° C., and 45° C. Conducted a 72 hour light test. Compared colors to a 5° C. sample.

RESULTS: Acceptable Product

EXAMPLE 7

Gly-oxide dentifrice

Purpose: To prepare flavored samples for flavor stability testing.

| FORMULA | % w/w | BATCH |
|---|---|---|
| $H_2O_2$ | 11.5 | 575 |
| Citric Acid, Anhy. | 0.5 | 25 |
| Sodium Citrate, Dihy. | 1.5 | 75 |
| Pluronic F127 | 25.0 | 1250 |
| NaF | 0.2 | 10.0 |
| Flavor - See Below | 1.25 | 62.5 |
| Sodium Saccharin | 0.2 | 10.0 |
| Water DI, Filtered | 60.5 | 3002.5 |
| TOTAL | 100.0 | 100.0 |

Method: (1) Dissolve Citric Acid and Sodium Citrate, and NaF in the water (also add Na Saccharin); (2) Disperse the Pluronic F127 and place in freezer overnight; (3) When the Pluronic is dissolved, add the $H_2O_2$, mix well and divide into eight 592.5g sublots; (4) Add 7.5g of each individual flavor to sublots and mix well; (5) Package in Glaminate tubes (30–40g/tube); (6) Place on test at R.T., 37° C. & 45° C.; and (7) Test flavor stability weekly for four months.

FLAVORS

A. Glyoxide #48692
B. Florasynth #5018
C. Felton Lime S/R76753
D. Monsanto #8201
E. PFC 9610
F. Ferron #999
G. Felton #333
H. Unger #10173 "ANISE-MINT"

A. Some RT samples swollen and some exude product when opened. Tubes were very full.
C. No tubes swollen and no tubes exude product.

EXAMPLE 8

Gly-oxide dentifrice

Purpose: Prepare product for stability testing.

| FORMULA | % w/w | BATCH |
|---|---|---|
| Hydrogen Peroxide, 35% | 11.5 | 230 g |
| Citric Acid, Anhy. | 0.5 | 10 |
| Sodium Citrate, Dihy. | 1.5 | 30 |
| Pluronic F127 | 25.0 | 500 |
| Sodium Fluoride | 0.2 | 4 |
| Sodium Saccharin | 0.2 | 4 |
| Water, DI, Filtered | 61.1 | 1222 |
| TOTAL | 100.0 | 2000 |

Method: (1) Prepare the following solution:

| Citric Acid | 12.5 g | Pass through |
| NaCitrate | 37.5 | a 0.2 Angstrom |
| NaF | 5.0 | Filter Reserve |
| Na Saccharin | 5.0 | 1270 g for use |
| Water, DI, Filt. | 1527.5 | in Step 2 (below) |
| TOTAL | 1587.5 | |

(2) Charge a beaker with 1270 g of above with mixing and add Pluronic. Mix in ice both until dissolved; (3) Add $H_2O_2$ and mix well; (4) Fill into glaminate tubes; (5) Place on stability test at R.T., 37° C., 45° C., 55° C., and 65° C.

RESULTS: Acceptable Stability.

EXAMPLE 9

Gly-oxide dentifrice
Purpose: Material for flavor experiments.

| FORMULA | % w/w | BATCH |
|---|---|---|
| 1. $H_2O_2$, 35% | 11.5 | 287.5 |
| 2. Citric Acid, Anhy. | 0.5 | 12.5 |
| 3. Sodium Citrate, Dihy. | 1.5 | 37.5 |
| 4. Pluronic F127 | 25.0 | 625.0 |
| 5. NaF | 0.2 | 5.0 |
| 6. Na Saccharin | 0.2 | 5.0 |
| 7. Water, DI, Filtered | 61.3 | 1532.5 |

| FORMULA | % w/w | BATCH |
|---|---|---|
| TOTAL | 00.0 | 2500 |

Method: (1) Dissolve 2, 3, 5, and 6 in 7. Pass through a 0.2 μ Millipore filter; (2) Disperse 4 in above and solubilize by the cold method; (3) Add $H_2O_2$ and mix well; and (4) Divide into four 1000 ml sub lots.

Resulting material is identified as Example 9 Base for use in Example 10.

EXAMPLE 10

Gly-oxide dentifrice

Purpose: To prepare Gly-oxide dentifrice flavored with menthol, eucalyptol, and gly-oxide flavor.

| FORMULA | A | B | C | D |
|---|---|---|---|---|
| EX. 9 Base | 98% w/w | 97 | 97.5 | 96.5 |
| Menthol 20% in Ethanol | 2 | 2 | 2 | 2 |
| Gly-Oxide Flavor | | 1 | | 1 |
| Eucalyptol | | | 0.5 | 0.5 |
| TOTAL | 100 | 100 | 100 | 100 |

Method: (1) Prepare Gly-Oxide base as shown. See Example 9; (2) with mixing, add flavoring ingredients to the base in sequence appearing above; mix well; and (3) Fill Glaminate tubes c 40 ml each and seal on the Vertrod unit. When Menthol was added, product changed to a white color but no ppt was seen (i.e., particles). The product has the typical $H_2O_2$ flavor.

EXAMPLE 11

Gly-oxide dentifrice
Purpose: To prepare product containing xylitol.

| FORMULA INGREDIENTS | % w/w | BATCH |
|---|---|---|
| 1. $H_2O_2$, 35% | 11.5 | 57.5 g |
| 2. Citric Acid, Anhy. | 0.5 | 2.5 |
| 3. Na Citrate, Dihy. | 1.5 | 7.5 |
| 4. Pluronic F127 | 25.0 | 125.0 |
| 5. NaF | 0.2 | 1.0 |
| 6. Xylitol - Xylo-Pentane - 1,2,3,4,5 - Pentol | 20.0 | 100.0 |
| 7. $H_2O$, Filtered, DI | 41.3 | 206.5 |

| FORMULA INGREDIENTS | % w/w | BATCH |
|---|---|---|
| TOTAL | 100.0 | 500.0 |

Method: (1) Dissolve 2, 3, 5, and 6 in 7; (2) Disperse 4 in above and freeze; (3) Mix well and add 1; This was done in an ice bath, and the product was a thick viscous gel at this stage. It is believed the 20% xylitol acts as a thickener and some Pluronic F127 can be removed from the formula RESULTS: Product is acceptable.

EXAMPLE 12

Gly-oxide dentifrice

Purpose: To prepare flavored product for toxicology and for stability test.

| INGREDIENT LOT | A | B | C | D | E | F |
|---|---|---|---|---|---|---|
| $H_2O_2$, 35% | 11.5 w/w | | | | | |
| Citric Acid, Anhy. | 0.5 | | | | | |
| Na Citrate, Dihy. | 1.5 | | | | | |
| Pluronic F 127 | 25.0 | | | | | |
| NaF | 0.2 | | | | | |
| Na Saccharin | 0.2 | | | | | |
| Felton Lime Terpenes Art. | — | 1.25 | | | | |
| Felton Mint Blend #006 | — | — | 1.00 | | | |
| Felton Mint Blend #006A | — | — | — | 1.00 | | |
| Gly-Oxide Flavor | — | — | — | — | 1.25 | |
| Menthol (20% w/w in E & OH) | — | — | — | — | — | 1.00 |
| Eucalyptol | | | | | | 0.25 |
| Water, DI, Filtered | 61.1 | 59.85 | 60.1 | 60.1 | 59.85 | 59.85 |
| TOTAL | 100 | 100 | 100 | 100 | 100 | 100 |

Method: (1) Dissolve Citric Acid, Na Citrate, Na Fluoride, and Na Saccharin in water (2) Disperse Pluronic F127 and dissolve by cold method; (3) With mixing, add $H_2O_2$ and then flavor if called for; and (4) After mixing to insure the product to be homogeneous, fill into tubes by hand and seal on a Vertrod (4H/HTV/SP) dwell @ 7 and heat @ 8.

Results: All products were acceptable gels at room temperature. All contained bubbles.

EXAMPLE 13

Gly-oxide dentifrice

Purpose: Prepare Pluronic—water gels at 23% and 24% w/w. Determine the viscosity using a Brookfield viscometer.
Results:

| SAMPLE # | 23% | 24% |
|---|---|---|
| 1 | 7,840 cps | 104,800 |
| 2 | 7,840 | 121,800 |
| 3 | 10,520 | 112,600 |
| 4 | 13,080 | 124,800 |
| 5 | 10,040 | 108,000 |
| X | 9,864 | 114,400 |

The temperature of these gels was 21–22° C. at the time of measurement. THe 23% gels were very viscous but pourable products. THe 24% gels were ringing gels.

EXAMPLE 14

Gly-oxide dentifrice

| INGREDIENTS | LOT | A | B | C | D | E | F |
|---|---|---|---|---|---|---|---|
| Urea - Peroxide | 20% sol. | 50% w/w | 50 | 50 | 50 | 50 | 50 |
| NaF | | 0.2 | | | | | |
| Pluronic F127 9997 | | 10 | 15 | 20 | 22 | 10 | 10 |
| Carbopol 934 47825 | | | | | | 0.5 | |
| Natrosol250MR 10220 (Alkali soluble cellulose ether) | | | | | | | 2.5 |
| $KH_2PO_4$ | | .675 | | | | | |
| NaOH | | 1.75 | | | | | |
| Glycerine | | 10 | | | | | |
| Methyl Paraben | | .09 | | | | | |
| Propyl Paraben | | .06 | | | | | |
| Na Saccharin | | .02 | | | | | |
| Flavor | | | | | | | |
| Color | | | | | | | |
| $H_2O$ | QS | 28.6 | 23.6 | 18.6 | 16.6 | 28.1 | 26.1 |
| TOTAL | | 100 | 100 | 100 | 100 | 100 | 100 |

Method: (1) Dissolve parabens in glycerine with heat—heat to 30° C.; (2) Dissolve NaF, $KH_2PO_4$, NaSac. in $H_2O$ (i.e., $H_2O$ in place of Urea-Peroxide) @5° C. Keep beaker in ice bath to maintain temp. at 0–10° C.; (3) with mixing add Pluronic; (4) When dissolved, add Carbopol 934 if called for and dissolve with mixing; (5) If called for add Natrosol 250 M5 to step 1 and slurry; (6) with continued mixing (in ice-bath) add step 1 or 5 to step 3 or 4; (7) Adjust pH to 6.0 [NOTE: with Carbopol and Natrosol must stabilize before neutralization]; (8) Bring to weight with $H_2O$; (9) Remove from re-bath and allow to come to RT.

Results: A and B—clear solutions, colorless but thin. C and D—clear, colorless ringing gels of suitable viscosity to use as a dentifrice. Taste not unpleasant. E—product not acceptable. Can be made acceptable by buffering. F—product not acceptable.

EXAMPLE 15

Gly-oxide dentifrice

| FORMULA | % w/w | GM/1500 gm |
|---|---|---|
| 1. Hydrogen Peroxide 90% | 4.50 | 67.5 gm |
| 2. Citric Acid, hydrous | 0.55 | 8.25 gm |
| 3. Sodium Citrate hydrous | 1.50 | 22.5 gm |
| 4. Pluronic F127 | 25.00 | 375.0 gm |
| 5. Sodium Fluoride | 0.20 | 3.0 gm |
| 6. Sodium Saccharin | 0.30 | 4.5 gm |
| 7. Felton Artificial Mint Blend 006 | 1.25 | 18.75 gm |
| 8. Filtered DI water | 66.70 | 1000.0 gm |
| TOTAL | 100 | 14995.0 gm |

Method:
(A) Dissolve items 1,2,3,5,6 in DI water.
(B) Disperse item 4 and put into freezer overnight.
(C) Thaw to liquid state and add item (7) with mixing.
(D) Pour into tubes and allow to come o gel.
(E) Heat seal the tubes.

Result: Acceptable Product.

EXAMPLE 16

Gly-oxide dentifrice

Purpose: To make a toothpaste.

| FORMULA | % w/w | Per 2150 pw |
|---|---|---|
| Citric Acid, Anhydrous | 0.5 | 10.75 gm |
| Sodium Citrate, hydrous | 1.5 | 32.25 gm |
| Pluronic F-127 | 25.0 | 537.50 gm |
| Sodium Fluoride | 0.2 | 4.3 gm |
| Sodium Saccharin | 0.2 | 4.3 gm |
| Glyoxide Flavor | | |
| Hydrogen Peroxide 35% | 11.43 | 245.0 gm |
| DI Water | 60.17 | 1294.0 gm |
| TOTAL | 99.0 | 2128.1 gm |

Method: (1) dissolve Citric Acid, Sodium Citrate, Sodium Fluoride, and Saccharin in water; (2) Disperse Pluronic F-127 in Step 1 and dissolve by the cold method (place in refrigerator overnight and complete solution by mixing the product with the vessel immersed in an ice bath); (3) Continue mixing and add $H_2O_2$ and the flavor if called for; (4) Fill by hand into 400.00 gm Jar.

Note:
BATCH A
1000 gm of unflavored sample
5 gm of Glyoxide flavor (mouth wash flavor type #1)
BATCH B
1000 gm of unflavored sample
10 gm of Glyoxide flavor (mouth wash flavor type H/)

Result: Acceptable Product.

TABLE 1

| RANGE OF CONCENTRATIONS | |
|---|---|
| INGREDIENTS | % w/w |
| Urea Peroxide | 10 |
| NaF | 0.2 |
| Pluronic Surfactant | 10–22, 18, 28, 28, 25, 15 |
| Carbopol thickening agent | 0.5, 6.5, 1.2 |
| Natrosol | 2.5 |
| $KH_2PO_4$ (Potassium Phosphate) buffering agent | 0.675 |
| NaOH (caustic soda) | 0.175, 0.155 |
| Glycerine | 10 |
| Methyl Paraben | 0.09 |
| Propyl Paraben | 0.06 |
| Na Saccharine | 0.2, 0.3 |
| $H_2O$ | 11.5, 16.6, 28.6, 35.02, 10.82–20.77, 61.1, 55.25, 51.6 30.8, 41.3, 63.5, 56.3 |
| Flavors | 1.25 |
| Urea | 6.83 |
| $H_2O_2$ | 4, 11.5, 20 |

TABLE 1-continued

| RANGE OF CONCENTRATIONS | |
|---|---|
| INGREDIENTS | % w/w |
| Triethanolamine | 12% (0.75, 1.0, 1.25, 1.5) |
| Xylitol | 20 |

In an additional embodiment of the invention, from 0.5% to 5% by weight, sodium lauryl sulfate is added to the above composition to produce a foam dentrifice.

The foregoing description merely explains and illustrates the invention and the invention is not limited thereto except insofar as those who have the invention before them are able to make modifications and variations therein without departing from the scope of the invention.

What is claimed is:

1. A non-abrasive aqueous oral gel composition comprising from about 0.5 to about 10% by weight of a urea peroxide compound and from about 0.01 to about 2% by weight of a compound providing fluoride or fluoride containing ions in said non-abrasive aqueous oral gel composition, wherein said fluoride compound reacts with said peroxide compound producing a pH stabilizing effect on said non-abrasive aqueous oral gel composition.

2. An oral composition as claimed in claim 1, wherein said urea peroxide comprises 0.5% to about 4% by weight of said oral composition.

3. An aqueous oral composition as claimed in claim 1 wherein said fluoride compound comprises about 0.2% by weight of said oral composition and said fluoride compound may be selected from one of the group consisting of sodium fluoride and stannous fluoride.

4. An oral composition as claimed in claim 1 and further including from about 10% to about 28% by weight non-ionic surfactant.

5. The oral composition as claimed in claim 4 wherein said non-ionic surfactant comprises a poloxamer compound.

6. An oral composition as claimed in claim 1 and further comprising from about 0.5% to about 6.5% by weight carboxypolymethylene for use as a thickening agent.

7. An aqueous oral composition as claimed in claim 1 and further comprising 0.5% to 3% by weight alkali soluble cellulose ethers for use as a viscosity increasing agent.

8. An oral composition as claimed in claim 1 and further comprising about 0.5% to about 1% by weight potassium phosphate for use as a buffering agent.

9. An oral composition as claimed in claim 1 and further comprising 0.1% to 0.5% by weight sodium hydroxide for use as a buffering agent with potassium phosphate.

10. An aqueous oral composition as claimed in claim 1 and further comprising from about 1% to about 20% by weight glycerine for use as a solvent.

11. An aqueous oral composition as claimed in claim 1 and further comprising about 0.01% to about 0.1% by weight methylparaben for use as a preservative.

12. An aqueous oral composition as claimed in claim 1 and further comprising from about 0.01% to about 0.1% by weight propylparaben for use as a preservative.

13. An aqueous oral composition as claimed in claim 1 and further comprising about 0.2% to about 0.3% by weight sodium saccharin for use as an artificial sweetener.

14. An aqueous oral composition as claimed in claim 1 and further comprising from about 11% to about 64% by weight filtered deionized water for use as a solvent.

15. An aqueous oral composition as claimed in claim 1 and further comprising about 0.25% to about 1.5% by weight flavoring agents, said flavoring agents selected from the group consisting of spearmint flavor, min flavor, sodium citrate, citric acid anhydrous, sodium citrate dihydrate, lime terpenes and methyl eucalyptol.

16. An aqueous oral composition as claimed in claim 6 and further comprising from about 1% to about 12% by weight triethanol-amine for use as a neutralizing agent.

17. An aqueous oral composition as claimed in claim 1 and further comprising from about to 10% to about 20% by weight xylitol for use as a sweetening agent.

18. An aqueous oral gel dentifrice composition comprising:
about 11½% ± 10% by weight urea peroxide compound said urea peroxide compound being in the form of a 35% urea peroxide solution ±15% and further comprising one or more of the group consisting of:
about 0.55% ± 0.05% by weight citric acid hydrous;
about 1½ ±1% by weight sodium citrate hydrous;
about 25% ± 10% by weight polyoxamer;
about 0.20% ± 0.1% by weight sodium fluoride;
about 0.30% ± 0.2% sodium saccharine;
about 1.25% ± 1% by weight mint flavoring;
about 59.70% ± 20% purified filtered water; and
wherein said dentifrice composition is pH stabilized by the reaction of said sodium fluoride with said urea peroxide.

19. An aqueous oral composition as claimed in claim 1, wherein said urea peroxide comprises about 4% by weight of said oral composition.

20. An aqueous oral composition as claimed in claim 1 and further comprising from about 0.5% to about 5% by weight sodium lauryl sulfate as a foaming agent so as to provide a foam dentifrice.

* * * * *